United States Patent
Horstmann et al.

(10) Patent No.: US 10,301,252 B2
(45) Date of Patent: May 28, 2019

(54) PRODUCTION OF TERT-BUTYL ESTERS OF ETHYLENICALLY UNSATURATED CARBOXYLIC ACIDS

(71) Applicant: BASF SE, Ludwigshafen am Rhein (DE)

(72) Inventors: Catharina Horstmann, Ludwigshafen am Rhein (DE); Claus Hechler, Ludwigshafen am Rhein (DE); Gregor Grackiewicz, Ludwigshafen am Rhein (DE); Bernd Schall, Ludwigshafen am Rhein (DE)

(73) Assignee: BASF SE, Ludwigshafen Am Rhein (DE)

( * ) Notice: Subject to any disclaimer, the term of this patent is extended or adjusted under 35 U.S.C. 154(b) by 0 days.

(21) Appl. No.: 16/062,359

(22) PCT Filed: Nov. 28, 2016

(86) PCT No.: PCT/EP2016/079025
§ 371 (c)(1),
(2) Date: Jun. 14, 2018

(87) PCT Pub. No.: WO2017/102297
PCT Pub. Date: Jun. 22, 2017

(65) Prior Publication Data
US 2019/0002389 A1    Jan. 3, 2019

Related U.S. Application Data

(60) Provisional application No. 62/267,331, filed on Dec. 15, 2015.

(30) Foreign Application Priority Data

Dec. 15, 2015    (DE) .................. 10 2015 121 860

(51) Int. Cl.
*B01D 3/00*    (2006.01)
*B01D 3/14*    (2006.01)
(Continued)

(52) U.S. Cl.
CPC .............. *C07C 67/54* (2013.01); *B01D 3/009* (2013.01); *B01D 3/143* (2013.01); *B01D 5/006* (2013.01);
(Continued)

(58) Field of Classification Search
CPC ............................... C07C 67/54; B01D 3/009
(Continued)

(56) References Cited

U.S. PATENT DOCUMENTS 3,031,495 A    4/1962    Young et al.
3,037,052 A    5/1962    Bortnick
(Continued)

FOREIGN PATENT DOCUMENTS

DE    1128428 B    4/1962
DE    1249857 B    9/1967
(Continued)

OTHER PUBLICATIONS

International Search Report for PCT/EP2016/079025 dated Mar. 1, 2017.
(Continued)

*Primary Examiner* — Deborah D Carr
(74) *Attorney, Agent, or Firm* — Drinker Biddle & Reath LLP

(57) ABSTRACT

A process for continuously preparing the tert-butyl ester of an ethylenically unsaturated carboxylic acid, by a) reacting an ethylenically unsaturated carboxylic acid with isobutene in the presence of an acidic catalyst to give an esterification mixture; b) removing the acidic catalyst; c) removing low-
(Continued)

boiling components; and d) supplying a tert-butyl ester-comprising liquid to a distillation apparatus and subjecting it to purifying distillation in the distillation apparatus, where d1) in the distillation apparatus the tert-butyl ester-comprising liquid is separated into a tert-butyl ester-comprising gaseous top product and a carboxylic acid-comprising liquid bottom product; d2) the tert-butyl ester-comprising gaseous top product is at least partly condensed and the condensate is recycled partly as reflux to the distillation apparatus; d3) the carboxylic acid-comprising liquid bottom product is recycled at least partly to step a); d4) carboxylic acid-comprising liquid bottom product is drawn off and passed to a heater; a superheated, liquid recycle stream is taken from the heater; and the superheated recycle stream is let down into the distillation apparatus; and d5) at least in the top region of the distillation apparatus, the distillation apparatus walls in contact with the vapor, at least in sub-regions, are heated and/or thermally insulated. In the course of the process, the separation of the tert-butyl ester from unreacted carboxylic acid is carried on with a particularly low level of accompanying polymerization both of the tert-butyl ester and of the carboxylic acid.

14 Claims, 5 Drawing Sheets

(51) Int. Cl.
*B01D 5/00* (2006.01)
*C07C 67/02* (2006.01)
*C07C 67/04* (2006.01)
*C07C 67/54* (2006.01)
*C07C 67/62* (2006.01)
*C07C 69/54* (2006.01)

(52) U.S. Cl.
CPC .............. *C07C 67/02* (2013.01); *C07C 67/04* (2013.01); *C07C 67/62* (2013.01); *C07C 69/54* (2013.01); *B01D 3/148* (2013.01); *Y02P 20/127* (2015.11)

(58) Field of Classification Search
USPC .......................................................... 560/205
See application file for complete search history.

(56) References Cited

U.S. PATENT DOCUMENTS

| | | |
|---|---|---|
| 3,082,246 A | 3/1963 | Chafetz |
| 3,087,962 A | 4/1963 | Bortnick |
| 3,088,969 A | 5/1963 | Callahan et al. |
| 3,167,578 A | 1/1965 | Fernbolz et al. |
| 5,897,749 A | 4/1999 | Kroker et al. |
| 6,756,506 B2 | 6/2004 | Kroker et al. |
| 6,998,026 B2 | 2/2006 | Kroker et al. |
| 7,745,658 B2 | 6/2010 | Lipowsky et al. |
| 10,023,520 B2 | 7/2018 | Horstmann et al. |
| 2013/0098752 A1 | 4/2013 | Castillo-Welter et al. |

FOREIGN PATENT DOCUMENTS

| | | | |
|---|---|---|---|
| DE | 3105399 A1 | 10/1982 | |
| DE | 19539295 A1 | 4/1997 | |
| DE | 102008002923 A1 * | 1/2009 | ............. C07C 67/04 |
| EP | 268999 A2 | 6/1988 | |
| GB | 934917 A | 8/1963 | |
| WO | WO-0210109 A1 | 2/2002 | |
| WO | WO-0210110 A2 | 2/2002 | |
| WO | WO-2011110257 A2 | 9/2011 | |

OTHER PUBLICATIONS

Written Opinion of the International Searching Authority for PCT/EP2016/079025 dated Mar. 1, 2017.
Transmittal of Interntal Preliminary Report on Patentability for International Application No. PCT/EP2016/079025, dated Jun. 21, 2018.

* cited by examiner

PRODUCTION OF TERT-BUTYL ESTERS OF ETHYLENICALLY UNSATURATED CARBOXYLIC ACIDS

CROSS-REFERENCE TO RELATED APPLICATIONS

This application is a national stage application (under 35 U.S.C. § 371) of PCT/EP2016/079025, filed Nov. 28, 2016, which claims benefit of U.S. Application No. 62/267,331, filed Dec. 15, 2015, and German Application No. 102015121860.7, filed Dec. 15, 2015, all of which are incorporated herein by reference in their entirety.

The present invention relates to a continuous process for preparing the tert-butyl ester of an ethylenically unsaturated carboxylic acid by reacting the carboxylic acid with isobutene.

The tert-butyl esters of ethylenically unsaturated carboxylic acids have a variety of uses. tert-Butyl (meth)acrylates, for example, are important starting materials for preparation of polymers which are used, inter alia, as a constituent of paints, adhesives or coating resins. tert-Butyl esters of this kind are generally prepared by acid-catalyzed addition of a carboxylic acid onto isobutene (Houben-Weyl, Methoden der Organischen Chemie [Methods of Organic Chemistry], vol. 8, 1952, p. 534; U.S. Pat. Nos. 3,031,495 and 3,082,246). Catalysts used are acids soluble in the reaction mixture, for example mineral acids or alkyl- or arylsulfonic acids (DE-A-12 49 857, U.S. Pat. Nos. 3,087,962, 3,088,969), or insoluble catalysts such as acidic exchanger resins (U.S. Pat. Nos. 3,037,052, 3,031,495, DE-A-31 05 399, EP-A-268 999).

WO 02/10109 A1 describes a process for continuously preparing the tert-butyl ester of an aliphatic $C_1$-$C_4$ carboxylic acid by reacting the carboxylic acid with isobutene in the liquid phase in the presence of an acidic catalyst in a reactor, the ester being recovered by distillation from the reaction mixture obtained after removal of the unconverted isobutene and the low boilers.

WO 02/10110 A2 describes a process for preparing a tert-alkyl (meth)acrylate by reacting (meth)acrylic acid with an olefin in a homogeneous phase in the presence of an acidic catalyst and removing the tert-alkyl (meth)acrylate by distillation from the reaction mixture, obtained following removal of the unconverted isobutene and the low boilers.

Particularly, at relatively high temperature, ethylenically unsaturated carboxylic acids and their esters may display a strong propensity toward polymerization. Particularly in distillations, these compounds are generally subject to temperatures which can easily trigger unwanted polymerization. A consequence of any such polymerization is the fouling of the apparatus, the clogging of lines and pumps, and the covering of column trays and heat exchanger surfaces. Cleaning the plants is a laborious, expensive and environmentally burdensome operation, and greatly reduces plant availability. Furthermore, uncontrolled radical polymerizations may represent a safety risk.

It is an object of the present invention, therefore, to provide a process for continuous preparation of the tert-butyl ester of an ethylenically unsaturated carboxylic acid that accomplishes the separation of the tert-butyl ester from unconverted carboxylic acid while avoiding as far as possible the polymerization both of the tert-butyl ester and of the carboxylic acid.

WO 2011/110257 A2 describes a method for obtaining a readily polymerizable compound such as (meth)acrylic acid from a liquid composition by distillation in a distillation apparatus, the lower part of the distillation apparatus seeing the drawing-off of a recycle stream, which as a superheated, liquid recycle stream is let down into the distillation apparatus. The readily polymerizable compound is separated in this way from—for example—solvents.

WO 2011/110257 A2 does not describe the removal of an ethylenically unsaturated ester from unconverted ethylenically unsaturated carboxylic acid. This distillative separation of two readily polymerizable compounds is more demanding, since the compositions obtained in the separation must be sufficiently polymerization inhibited over the entire distillation apparatus. Furthermore, by comparison with lower esters, tert-butyl esters are relatively high-boiling, thereby raising the thermal load in the distillation.

DE 10 2008 002 923 A1 describes a process for preparing tertiary alkyl esters of (meth)acrylic acid from (meth)acrylic acid and an olefin, in which the (distillative) removal of the ester from the (meth)acrylic acid takes place with stabilization by an N-oxyl compound.

DE 195 392 95 A1 describes a method for continuous distillative separation of liquid mixtures whose main constituent is (meth)acrylic acid in a distillation apparatus. A substream of the liquid passed into the distillation apparatus is withdrawn and returned in superheated form into the distillation apparatus. The purified (meth)acrylic acid is withdrawn from the top of the distillation apparatus.

Applications for copolymers of tert-butyl (meth)acrylate include the production of coating formulations which cure with crosslinking and which are employed, for example, as vehicle paints or refinish paints. For this application a low acid content is desired.

The object is achieved by a process for continuously preparing the tert-butyl ester of an ethylenically unsaturated carboxylic acid, by a) reacting an ethylenically unsaturated carboxylic acid with isobutene in the presence of an acidic catalyst to give an esterification mixture;
b) removing the acidic catalyst;
c) removing low-boiling components; and
d) supplying a tert-butyl ester-comprising liquid to a distillation apparatus and subjecting it to purifying distillation in the distillation apparatus, where
  d1) in the distillation apparatus the tert-butyl ester-comprising liquid is separated into a tert-butyl ester-comprising gaseous top product and a carboxylic acid-comprising liquid bottom product;
  d2) the tert-butyl ester-comprising gaseous top product is at least partly condensed and the condensate is recycled partly as reflux to the distillation apparatus;
  d3) the carboxylic acid-comprising liquid bottom product is recycled at least partly to step a);
  d4) carboxylic acid-comprising liquid bottom product is drawn off and passed to a heater; a superheated, liquid recycle stream is taken from the heater; and the superheated recycle stream is let down into the distillatiuon apparatus; and
  d5) at least in the top region of the distillation apparatus, the distillation apparatus walls in contact with the vapor, at least in sub-regions, are heated and/or thermally insulated.

A bottom product is understood to be a liquid product which is withdrawn in the lower part of the distillation apparatus—for example, a liquid phase withdrawn at the geodecally lowest point of the distillation apparatus or from the one to three trays lying immediately above said point. A top product is understood to be a gaseous or liquid product which is taken off in the upper part of the distillation apparatus—for example, a liquid phase taken off at the top of the distillation apparatus or at the one to three trays situated immediately below the top.

In the course of the heating and recycling of the liquid bottom product removed, as carried out in accordance with the invention, the formation of a free gas-vapor space is avoided throughout the line path to and from the heater. Accordingly, gas phases which may condense in the line pathway and may form unstabilized liquid phases susceptible to polymerization, are essentially avoided.

In the process of the invention, furthermore, the walls which are in contact with the vapor, at least in the top region of the distillation apparatus, are thermally insulated and/or heated at least in subregions. As a result of this measure, the temperature of the walls within this region is held preferably above the condenstion temprature of the tert-butyl ester. In this way, condensation of the vapor on the walls, which may cause formation of unstabilized liquid phases susceptible to polymerization, is avoided.

The top region of the distillation apparatus refers to the region free from internals that lies above the topmost tray or above the topmost layer of packing. It is generally formed by a domed base (hood, e.g. dished end or torispherical end), which forms the capping element of the distillation apparatus.

The condensation temperature of a compound refers to the temperature from which the compound condenses at a given pressure, i.e. is converted from the gaseous state of matter into the liquid state.

In the esterification, an ethylenically unsaturated carboxylic acid is reacted with isobutene in the presence of an acidic catalyst to give an esterification mixture. The ethylenically unsaturated carboxylic acid is preferably selected from acrylic acid, methacrylic acid, dimethylacrylic acid, ethylacrylic acid, allylacetic acid, vinylacetic acid and vinylpropionic acid. In a preferred embodiment, the carboxylic acid is acrylic acid or methacrylic acid, particular preference being given to methacrylic acid.

In a preferred embodiment, the ethylenically unsaturated carboxylic acid has an acetic acid content of less than 300 ppm, more preferably less than 100 ppm, very preferably less than 20 ppm, and a propionic acid content of less than 300 ppm, more preferaly less than 200 ppm, very preferably less than 130 ppm. Since acetic acid and propionic acid can be removed from the tert-butyl ester in the further process only with great effort and cost, it is preferred to use ethylenically unsaturated carboxylic acid with a controlled acetic and/or propionic acid content, if the aim is to obtain an ethylenically unsaturated tert-butyl ester with a specified acetic and/or propionic acid content. The acetic and propionic acid content is determined customarily by means of gas chromatography.

The esterification is generally effected in the absence of a solvent and in the liquid phase. Catalysts used are therefore those which are at least partly soluble in the reaction mixture. Suitable catalysts are strong inorganic or organic acids. Strong inorganic acids are, for example, mineral acids such as sulfuric acid, phosphoric acid and polyphosphoric acid, preferably sulfuric acid. Strong organic acids are, for example, sulfonic acids such as p-toluene-, benzene-, dodecylbenzene- and methanesulfonic acid, preferably p-toluenesulfonic acid and methanesulfonic acid. The inorganic catalysts in particular are only partly soluble in the reaction mixture on commencement of the reaction. In the course of the reaction, the solubility of the catalyst improves (primarily because of the formation of a partial ester of the catalyst, for example the sulfuric monoester). At least in the last section, it is therefore generally in solution in the reaction mixture.

The concentration of the catalyst in the esterification mixture is generally about 0.1% to 10% by weight, preferably 0.5% to 5% by weight, based on the total amount of the esterification mixture.

The reaction of the ethylenically unsaturated carboxylic acid with isobutene in the presence of an acidic catalyst is effected preferably in conventional reaction vessels or in columns (DE-A-11 28 428). A suitable reactor is described by way of example in WO 02/10109 A1.

Preferably, the reaction is conducted in a reactor, which is especially a cylindrical reactor. The reactor is divided into a plurality of, preferably 3, 4 or 5, separate sections. The sections are separated from one another by dividing walls which run at right angles to the longitudinal axis of the reactor. Each of these has at least one orifice in order to enable the passage of the reaction mixture from one reactor section to the next. The number of orifices per dividing wall is guided by the size of the reactor. Preferably, the dividing walls have one orifice which is especially present in the middle of the dividing wall. The total area of the orifices per dividing wall is about 1/2000 to 1/500 of the cross-sectional area of the reactor.

The volume of the reactor sections may be the same or different. Preferably, the volume of the first reactor section is greater than that of the remaining sections. In the case of a reactor having four sections, the following proportions of the individual sections in the total reactor volume have been found to be preferable:

Reactor section 1 25% to 50%
Reactor section 2 10% to 25%
Reactor section 3 10% to 25%
Reactor section 4 25% to 50%

The reactor sections may advantageously be equipped with internals in order to improve the mixing of the reaction volume. Suitable internals are, for example, static mixing elements and internals having similar effects, such as grids, distributor plates or sieve plates. It is particularly preferable to equip the first reactor section with internals of this kind, which are then provided there especially in the upper half of the reactor section.

The carboxylic acid is fed into the first section of the reactor in liquid form, especially in the region of the base of the reactor. The feeding can be effected directly, for example via an immersed tube, but it is preferable to provide means which enable homogeneous distribution and mixing of the feedstocks. Means of this kind are known to those skilled in the art, for example distributor plates, perforated plates and tubes, nozzles, etc. The carboxylic acid is preferably fed in via a nozzle which brings about the mixing of a gas and a liquid and the mixing of the reactor contents. It is preferably disposed at the base of the reactor. Suitable nozzles are known to those skilled in the art (jet nozzle, mixing nozzle, two-phase nozzle, etc.) and are described, for example, in Ullmann's Encyclopedia of Industrial Chemistry, vol. B4, 5th edition, 1992, p. 280. Especially when a nozzle of this kind is used, the flow in the first two reactor sections is turbulent, but is essentially laminar in the downstream reactor sections. This allows the cascading of reaction sections of different characteristics, for example turbulent with high backmixing as in the stirred tank type, or laminar with low backmixing as in the tubular reactor type, which allows particularly advantageous configuration of the respective reaction section.

The catalyst is fed in in a mixture with the carboxylic acid, it being possible to employ fresh catalyst or recovered catalyst or a mixture thereof.

It has been found to be advantageous to feed at least a portion of the liquid high boiler phase from the catalyst removal described hereinafter and/or at least a portion of the bottom product of the purifying distillation into the reactor. In this way, a majority of the acidic catalyst and of the unconverted carboxylic acid is recycled.

The isobutene can be fed in in liquid and/or gaseous form. It is preferably fed in via an annular tube having a plurality of outlet orifices.

A portion of the reaction mixture can be withdrawn from the first and/or second reactor section and recycled back into the section in question. This ensures better mixing of the reaction mixture. The substream is appropriately recycled via the abovementioned mixing nozzle into the first reactor section and/or via a further nozzle in the region of the orifice present in the dividing wall into the second reactor section. The further nozzle may be a nozzle of the type mentioned above for the mixing nozzle. Preference is given to using a conical nozzle. The latter is preferably arranged such that its exit opening is at about the level of the dividing wall which divides the first section from the second. For (closed-loop) control of the temperature, the particular substream withdrawn can be conducted through a heat transferer.

The resultant esterification mixture is withdrawn at the upper end of the reactor and sent to further workup. Unconverted gaseous isobutene accumulates in the upper region of the reactor. Preferably, organic compounds, such as unconverted carboxylic acid, which are condensable are condensed out of the isobutene-containing gas stream taken off at the upper end of the reactor and thus are freed of gases that are inert with respect to the esterification, such as air and butane. Unconverted isobutene dissolves partly in the constituents condensed out. The condensed organic compounds are then fed into the first reactor section in liquid form via the mixing nozzle for example.

The esterification temperature overall is in the range from about 10 to 40° C. It is preferably controlled in such a way that it is at its highest in the first reactor section. Preferably, the reaction temperature in the first reactor section is in the range from about 30 to 40° C. It is lower in the second section, preferably by about 5 to 15° C. The temperature in the sections that follow downstream of the second section may be the same or different. It is generally not higher than in the second section, preferably lower, especially by about 3 to 10° C. In the fourth section, it is generally as high as in the third section or about 1 to 5° C. lower. The temperature in the last reactor section is preferably in the range from about 10 to 25° C.

The temperature distribution in a reactor having 4 sections is preferably as follows:
1st section: 33 to 38° C.
2nd section: 23 to 28° C.
3rd section: 15 to 22° C.
4th section: 15 to 22° C.

The temperature in the 3rd and 4th sections may be the same or different.

Since the addition of carboxylic acids onto isobutene is exothermic, it is appropriate to adjust the reaction temperature by removing the heat of reaction, especially in the first two reactor sections. This is especially effected with the aid of heat exchangers which may be in external or internal configuration. Cooling of the reactor walls is also possible. It has been found to be appropriate to undertake the temperature control in the first two reactor sections with the aid of external heat exchangers, through which a substream of the reaction mixture present in the particular reactor section is conducted and recycled again.

The esterification can be conducted at reduced pressure, ambient pressure or slightly elevated pressure (100 to 300 mbar abs.), or preferably at elevated pressure (e.g. 0.5 to 3 bar).

The reaction mixture leaving the reactor comprises a high proportion of the desired ester. In addition, it comprises unconverted reactants, catalyst, stabilizer, esters of the catalyst acid and further minor by-products. The reaction mixture comprises only very small amounts of isobutene oligomerization product, generally <2% by weight, based on the reaction mixture First the acidic catalyst is removed from the esterification mixture. To remove the acid catalyst, the esterification mixture is preferably partially evaporated, giving a liquid high boiler phase comprising the acidic catalyst and a vapor comprising tert-butyl ester and isobutene. The liquid high boilder phase is generally at least partly recycled into the reactor.

The partial evaporation can be conducted in any desired manner, but is preferably conducted in two stages. The evaporation is generally effected at elevated temperature and under reduced pressure. The conditions are guided by the particular product desired. They are generally chosen such that the temperature is in the range from about 50 to 150° C. The pressure is adjusted such that the evaporation is rapid and gentle. The pressure is, for example, in the range from 10 to 200 mbar abs., more preferably in the range from 30 to 90 mbar abs., most preferably in the range from 50 to 70 mbar abs.

Any vacuum pumps are suitable for generation of the reduced pressure. To avoid contamination, it has been found to be useful to use lubricant oil-free pumps. Particular preference is given to using Roots vacuum pumps without lubricant oil and what are called dry-running screw vacuum pumps. Alternatively, it is possible to use liquid-ring pumps in which, for example, the target ester serves as barrier fluid.

The two-stage evaporation is preferably conducted in such a way that, in a first stage, 40% to 95% by weight, preferably 60% to 90% by weight, of the desired ester evaporates off. The vapor comprises, as well as the tert-butyl ester and carboxylic acid, the low-boiling constituents, such as tert-butanol, tert-butyl acetate and diisobutene. The bottoms obtained in the first distillation comprise, as first high boiler phase, essentially the residual tert-butyl ester, carboxylic acid, acidic catalyst and high-boiling constituents, for example polymeric (meth)acrylic compounds in the case of use of (meth)acrylic acid. 10% to 100% by weight of the first high boiler phase is fed to the second evaporation stage. If only a portion of the first high boiler phase is fed to the second evaporation stage, the remainder of the first high boiler phase is recycled into the reactor. In the second evaporation stage, the residual target ester and the majority of carboxylic acid (up to about 90% by weight) are evaporated off.

The bottoms of the second evaporation stage, as the second high boiler phase, comprise essentially the acidic catalyst, the residual carboxylic acid and high-boiling constituents. The second high boiler phase is discharged at least partly, preferably fully. However, it can also be partly recycled into the reactor. The vapors from the two stages are combined and condensed. The distillate contains generally <20 ppm, especially <10 ppm of catalyst.

Both evaporation stages can be conducted in customary apparatuses. Preference is given, however, to using apparatuses which allow rapid distillation, for example film evaporators. Suitable film evaporators are known to those skilled in the art; see, for example, Ullmann's Encyclopedia of Industrial Chemistry, 5th ed., vol. B3, 2-21 to 2-24 and 3-1 to 3-25, 1988.

Preference is given to using falling-film or falling-stream evaporators in the first evaporation stage, and thin-film evaporators having wipers or helical tube evaporators in the second stage.

It has been found to be particularly preferable to use a falling-film evaporator as described by way of example in WO 02/10110 in the first evaporation stage.

The vapor, which comprises essentially the target ester, carboxylic acid, and low-boiling constituents, such as tert-butanol, tert-butyl acetate and diisobutene, is customarily condensed. Condensation takes place preferably in one or more series-connected plate condensers or shell and tube condensers. Preference is given to using shell and tube condensers having vertical tubes through which the vapor flows from the top downward. Uncondensed vapor is preferably recycled to the reactor.

In one embodiment, the vapor is condensed in a two-stage condensation, in which a major amount of the ester is condensed at a first temperature and a further amount of the ester is condensed at a second temperature lower than the first temperature. As a result of this, the removal of the tert-butyl ester is very largely complete and is accompanied by minimal cocondensation of unconverted isobutene. The fractional condensation takes place preferably in two series-connected condensers.

To avoid solid deposits on the contact surfaces of the condenser, a substream of the collected condensate is appropriately circulated, in order to constantly purge the contact surfaces. The condensate pumped in circulation can be distributed homogeneously, for example, by means of a distributor, between the tubes of the shell and tube condenser and runs off down the inner walls of the condenser tubes. When polymerizable carboxylic acids are used, distribution of a stabilizer described in detail below is also achieved in this way.

The (combined) condensate of the vapor condensation is sent to a low boiler removal which is preferably operated distillatively. In the distillative low boiler removal, the low-boiling constituents, i.e. constituents other than isobutene having lower boiling points than the target ester, are preferably distilled off overhead. The low boiler removal also affords further amounts of unconverted isobutene which are preferably separated from the low-boiling constituents and are recycled into the step. Low boilers obtained in the preparation of tert-butyl methacrylate are, for example, tert-butyl acetate, tert-butanol and diisobutene.

For the removal of low boilers, condensate from the removal of catalyst is supplied to a low-boilers distillation column, in the bottom of which a liquid product freed from low boilers is obtained, and at the top of which a low boilers vapor is obtained. The liquid product freed from low boilers, comprising essentially target ester and carboxylic acid, is supplied for further workup. The low boilers vapor is condensed. Preferably the condensate is partly returned as a recycle stream to the top of the low-boilers distillation column.

Uncondensed low boilers vapor may still contain up to 5% by weight, based on the top product, of target ester. The low boilers vapor further comprises isobutene and is preferably supplied to the esterification.

The distillation temperature (liquid-phase temperature) in the low-boilers distillation column is generally in the range from 30 to 110° C. The pressure is selected according to the particular product. In the case of the preparation of tert-butyl methacrylate, for example, the pressure is in the range from 0.1 to 0.25 bar (abs).

Suitable low-boilers distillation columns include customary columns with random packings or structured packings or with bubble-cap, valve or sieve trays. Preference is given, however, to using a tray column having 30 to 50 dual-flow trays. The feed to the low boilers distillation column is generally in the middle region.

The low-boiling components are condensed preferably in one or more series-connected condensers, more particularly plate or shell and tube condensers. Preference is given to using shell and tube condensers having vertical tubes through which the vapor flows from the top downward.

Diisobutene is the main constituent of the low boilers removed. Diisobutene is a mixture of various isooctene isomers. The condensation points thereof are close together in practice. The reference point may, for example, be the condensation point of 2,4,4-trimethylpent-1-ene.

In one embodiment the low boilers vapor is condensed as a two-stage condensation, where a major amount of diisobutene is condensed at a first temperature and a further amount of diisobutene is condensed at a second temperature lower than the first temperature. The result of this is to maximize removal of the diisobutene while minimizing cocondensation of unconverted isobutene. The fractional condensation takes place preferably in two series-connected condensers.

Following the removal of the acidic catalyst (stage b) and of the low-boiling components (stage c) from the esterification mixture, the tert-butyl ester-comprising liquid is subjected to purifying distillation in a distillation apparatus (stage d).

In the purifying distillation, the tert-butyl ester-comprising liquid in the distillation apparatus is separated into a tert-butyl ester-comprising gaseous top product and a carboxylic acid-comprising liquid bottom product. The bottom product is at least partly and especially completely recycled into the esterification.

The distillation temperature is generally in the range from 40 to 130° C. The pressure is selected according to the ester to be distilled.

The distillation apparatus is customarily a distillation column, as for example a conventional tray column, such as a column having 30 to 50 dual-flow trays and feed in the middle column region, for example. The substantially pure target ester is removed via the top of the column. The process of the invention can be carried out as a continuous distillation, in a distillation column, for example, or else as a batchwise distillation, in a distillation still, for example.

In the purifying distillation, at least the walls in the top region of the distillation apparatus are heated and/or thermally insulated. As a result of the heating or thermal insulation of the walls in the top region, the condensation of gaseous products on the walls is prevented; such condensation may give rise to the formation of unstabilized liquid phases that are susceptible to polymerization.

The configuration of the distillation apparatus generally entails a hood which is connected via a flange to the cylindrical part of the distillation apparatus. The flange represents a cold bridge; accordingly, lower temperatures than in the remainder of the top region may prevail, with a consequent increased potential for condensation. Additional inhibition of polymerization is therefore advantageous at this location.

A polymerization inhibitor is metered preferably into the vapor pipe via which the tert-butyl ester-comprising gaseous top product is taken off from the distillation apparatus. Metering takes place preferably via a flow limiter, preferably one which allows fine distribution of liquid. Flow limiters used are preferably a baffle, a valve, a constriction, a perforated plate, a nozzle, a capillary, or combinations thereof, more particularly a nozzle. The use of a flow limiter allows improved distribution of the stabilizer at the walls in the top region of the distillation apparatus and also at the flange which connects the hood and the cylindrical part of the distillation apparatus.

Because of the different volatilities of the substances to be separated, concentration profiles are established over the length of the column. In the upper region of the distillation apparatus the tert-butyl ester is dominant, then, and in the lower region it is the unconverted ethylenically unsaturated carboxylic acid. Polymerization inhibitors used for stabilization also have different volatilities. The boiling point of the polymerization inhibitors is generally higher than that of the tert-butyl ester. Hence it may be the case that tert-butyl ester and/or carboxylic acid evaporate and condense at a cooler location in the distillation apparatus. The condensates here potentially lack adequate inhibition from polymerization. The formation of these condensates is prevented by the heating of the walls in the top region of the distillation apparatus, and/or by the thermal insulation of these walls. The fine distribution of the polymerization inhibitor in the vapor pipe, moreover, results in a more uniform distribution of the polymerization inhibitor on the walls in the top region of the distillation apparatus and hence results in fewer polymerization-susceptible condensates.

The walls in the top region of the distillation apparatus are preferably heated by bringing the region to be heated into thermal contact with a cladding system through which there is a flow of a heating medium, such as hot steam, for example.

The cladding system preferably comprises a jacket, a half-coil pipe, or trace heating hoses or lines, more particularly a half-coil pipe. A half-coil pipe is a pipe segment in halfshell form which is placed around the region to be heated and is welded to the outer wall of said region. The half-coil pipe is operated preferably with hot steam under a pressure of 1.2 to 2.5 bar, more preferably 1.3 to 1.7 bar, such as 1.5 bar, for example. Customarily the pressure can be regulated. The temperature is generally in the range from 105 to 130° C., preferably in the range from 108 to 113° C.

An alternative option is to use electrical heating, by means of heating wires or heating mats, for example.

The temperature of the walls in the top region of the distillation apparatus can also be kept above the condensation temperature of the tert-butyl ester by means of thermal insulation. Nevertheless, active heating of the walls in the top region of the distillation apparatus is preferred.

Thermal insulation of the walls in the top region of the distillation apparatus can be accomplished by application of customary insulating materials to the outer wall of the top region, such as (glass) wool, composite materials, panels or sheets, or pipes.

The temperature of the heated walls is preferably in the range from 2 to 20° C., more preferably 2 to 15° C., as for example 5 to 10° C., above the condensation temperature of the tert-butyl ester under the pressure which prevails in the distillation apparatus.

The tert-butyl ester-comprising gaseous top product is at least partly condensed. The condensate is partly recycled as reflux into the distillation apparatus. The other part of the condensate is discharged as product from the process.

The higher the reflux ratio in the distillation apparatus, the more effective the separation of ethylenically unsaturated carboxylic acid and the tert-butyl ester. The reflux ratio refers to the ratio between the amount of condensate of the tert-butyl ester-comprising gaseous top product that is recycled into the distillation apparatus and the amount of condensate of the tert-butyl ester-comprising gaseous top product that is conveyed further. Using a high reflux ratio, accordingly, a tert-butyl ester low in carboxylic acid can be obtained. A high reflux ratio, however, entails a high liquid-phase temperature and a relatively high thermal load on the ethylenically unsaturated carboxylic acid and tert-butyl ester. The reflux ratio is preferably in the range from 2 to 4, more preferably in the range from 2.5 to 3.5. The advantages of the process of the invention are manifested in particular under these conditions.

The overall amount of acetic acid, propionic acid and ethylenically unsaturated carboxylic acid in the end product is preferably less than 300 ppm, more preferably less than 200 ppm, very preferably less than 130 ppm. With particular preference the end product has an overall acid content of less than 300 ppm, more preferably less than 200 ppm, very preferably less than 130 ppm. For the determination of the acid content, the acid number is customarily determined by titrimetry and reported as methacrylic acid content.

The gaseous top product is condensed preferably in one or more series-connected condensers, more particularly plate condensers or shell and tube condensers. Preference is given to using shell and tube condensers with vertical tubes through which the vapor flows from the top downward.

Where an individual condenser is used, the pressure in the condenser is preferably in the range from 10 to 200 mbar abs., more preferably in the range from 30 to 100 mbar abs., very particularly in the range from 50 to 90 mbar abs. The temperature in the condenser is preferably 45 to 80° C., more preferably 50 to 65° C., below the condensation temperature of the tert-butyl ester under the pressure used. The temperature is preferably in the range from −25 to 0° C., more preferably in the range from −20 to −5° C.

The condensation temperature of tert-butyl acrylate at 60 mbar abs., for example, is 43° C. In this case the condenser is usefully used with brine cooling in operation.

In one embodiment the condensation of the gaseous top product takes place in the form of a two-stage partial condensation. This maximizes removal of the tert-butyl ester while minimizing cocondensation of low boilers which have not been removed. The two-stage partial condensation takes place preferably in two series connected condensers. The temperatures reported here for the partial condensations refer to the temperature of the condensate on withdrawal from the respective condenser.

The temperature of the coolant in the second condenser is lower by about 30 to 60° C. than that of the first condenser, in which the coolant has a temperature in the range from about 10 to 35° C.

The first temperature is preferably 0 to 45° C., more preferably 5 to 35° C., below the condensation temperature of the tert-butyl ester under the first pressure, and the second temperature is 45 to 80° C., preferably 50 to 65° C., very preferably 50 to 55° C., below the condensation temperature of the tert-butyl ester under the second pressure.

The second temperature is at least 5° C. below the first temperature. The second temperature is preferably at least 10° C., more preferably at least 20° C., very preferably at least 30° C. and most preferably at least 40° C. below the first temperature.

The first pressure is preferably in the range from 10 to 200 mbar abs., more preferably in the range from 30 to 100 mbar abs., very preferably in the range from 50 to 90 mbar abs. The second pressure is preferably in the range from 10 to 200 mbar abs., more preferably in the range from 30 to 100 mbar abs., very preferably in the range from 50 to 90 mbar abs. The first and second condensers are usually connected on the gas side. In that case the first and second pressures are the same.

The condensation temperature of tert-butyl acrylate at 60 mbar abs., for example is 43° C. In that case, river water or cooling water which has been brought to an equivalent temperature can be usefully used for cooling the first condenser, while the second condenser is used with brine cooling in operation.

The (combined) condensate is partially discharged as product from the process.

The carboxylic acid-comprising liquid bottom product is recycled at least partly into the esterification. The carboxylic acid-comprising liquid bottom product which is recycled into the esterification is cooled advantageously to a temperature in the range from 25 to 40° C., preferably 25 to 35° C. This is customarily performed using a warm water cooler which is operated at a temperature in the range from 25 to 35° C., such as at 30° C., for example.

Following the cooling, the substream of the bottom stream that is recycled into the esterification is guided preferably via a device for the removal of solid impurities. This device is preferably a filter. In this way, undissolved solid impurities, such as particles of polymer, for example, can be largely removed. Hence it is possible to prevent instances of clogging, such as in the lines for example. It is useful to provide the filter with a bypass line which can be connected in, in order to allow the filter to be removed for cleaning or for replacement without interruption to the process.

A further substream of the liquid bottom product is passed via a forced circulator evaporator, hence being drawn off and passed to a heater, from which a superheated liquid recycle stream is withdrawn and is let down into the distillation apparatus.

The pressure to which the liquid bottom product drawn off from the distillation apparatus, and recycled to the distillation apparatus, is subjected is increased by superheating. The superheated recycle stream is let down via a flow limiter. As a result of this, the liquid is superheated to above its boiling point in relation to the pressure in the interior of the distillation apparatus.

The passage of the superheated liquid through the flow limiter and its entry back into the distillation apparatus is accompanied by sudden evaporation of the liquid. This sudden evaporation, which is accompanied by a considerable increase in volume, results in an acceleration of the fluid stream entering the distillation apparatus, thereby reducing the risk of formation of deposits, for example of polymers at the entry point into the distillation apparatus. It is therefore advantage if the flow limiter is sited immediately ahead of the point of reentry of the superheated liquid into the distillation apparatus, or even in its interior.

In one embodiment the distillation apparatus here is operated in a manner known per se, with metered introduction of polymerization inhibitors (stabilizers) at suitable locations, as for example at the top of the distillation apparatus. In this way, the occurrence, in containers and pipelines which are not wetted with stabilizer solutions, of vapors of the readily polymerizable compound or of condensates of these vapors, is prevented.

It is advantageous that through operation of the evaporator in forced circulation, the resulting flow rate of the liquid in the heating apparatus, such as in the tube bundle of the heat exchanger, for example, is increased relative to operation with natural circulation. As a result, a continuous cleaning of the heat exchanger surfaces is achieved by the flowing product. A further advantage of the invention is the heat transition between heat exchanger and heated liquid that is improved as a result of the increased flow rate, this improved heat transition contributing in turn to the prevention of local instances of overheating.

In the implementation of the process of the invention, a conveying apparatus used is a pump, in order to allow the heater to be operated in forced circulation. This pump is preferably sited between the removal line and the heater, and so the pressure to the heater which follows in the flow direction is increased, in order to prevent the liquid evaporating downstream after said heater. A further pump may be used to take off the liquid stream of bottom product.

Preference is given to the addition, to the stream guided into the conveying apparatus, of an antifouling agent, selected for example from the succinimide derivatives sold under the KOMAD name, in order to protect this apparatus from contamination, clogging, or damage. In this way, undissolved solid impurities, such as particles of polymer, for example, can be largely removed before they are able to get into the heater and result there in instances of clogging.

Heaters used can be customary heat exchangers; preference is given to using a heat exchanger which operates in indirect heat exchange against a heating medium, more particularly a shell and tube heat exchanger. This heat exchanger is operated preferably in horizontal placement. Also possible is use of plate heat exchangers or spiral heat exchangers rather than shell and tube heat exchangers, since in that case, if appropriate flow rates and suppressed evaporation are maintained, the same advantages can be achieved as for the shell and tube heat exchanger.

The heating of the liquid taken off from the distillation apparatus using electrical energy is also possible.

Flow limiters used preferably comprise a baffle, a valve, a constriction, a perforated plate, a nozzle, a capillary, or combinations thereof, more particularly a valve. A rotary plug valve can be used, for example. It is particularly preferred if the opening characteristics of the flow limiter are adjustable. In this way, the pressure in the evaporator can always be kept above the boiling pressure of the liquid, relative to the pressure in the interior of the distillation apparatus, in the event of altered flow rates, as may occur, for example, during startup and shutdown operations.

In the steady state, the reactants are present in the reactor as a solution in the target ester, which allows homogenization of the reaction and particularly advantageous removal of heat. To start up the reactor, the reactor is therefore preferably filled with the target ester. Thereafter, the reactants and catalyst are introduced into the reactor and the reaction commences.

On startup of the plant, the reactor contents are preferably passed into a collecting vessel. The collecting vessel is disposed at the geodetically lowest point of the plant and is connected to the reactor via separate lines. In the case of a leak, rapid emptying of the reactor is thus possible. Typically, no pumping systems are needed for this purpose. The collecting vessel has a pressure equalization means and has been filled with an oxygenous gas having an oxygen content of 10% by volume of oxygen or less, preferably 5% by volume of oxygen or less, in inert gas, preferably nitrogen. The collecting vessel is cooled by means of a pump and an external heat exchanger. The contents of the collecting vessel can then be worked up further independently.

The reactants, especially the carboxylic acid, are preferably used in substantially anhydrous form. The surfaces in contact with the reaction components in the process preferably consist of materials matched to the corrosivity of the carboxylic acid used in terms of technical corrosion resistance, for example stainless steel of the 1.4541 or 1.4571 quality, or stainless steels at least equivalent to these in terms of corrosion characteristics. Because of the very low water content in the process system, even when strong inorganic acids are used as catalyst, there is no corrosive attack beyond the extent of the industrially relevant resistance in the case of these materials. In production plants for ethylenically unsaturated esters, it is typically necessary to clean with hot sodium hydroxide solution, as a result of which the materials used experience alternating stress between organic acid and sodium hydroxide cleaning medium. The use of what are called duplex steels such as 1.4462 may therefore be advantageous for improved long-term stability of the apparatus.

Especially in the regions where there are additionally also a high temperature and mechanical stress in addition to the described corrosive stress by inorganic acids and a strong inorganic acid as catalyst, as in the thin-film evaporator for removal of the acidic catalyst from the majority of the organic matter, it is advantageous to use materials having much better corrosion resistance, for example nickel-base materials such as 2.4602, 2.4605, 2.4610 or 2.4819. Not only has experience shown that these materials have a longer service life, but they additionally also have considerable reserves in the event of unplanned occurrence of water as corrosion-promoting agent because of even smaller rates of corrosive material removal compared to the stainless steels. The use of these materials allows advantageous emergency operation properties without any risk of rapid total loss of apparatuses. In a departure from standard operation, water may be present, for example, as a result of temporary unintentional introduction into the system, for example via water-contaminated feedstocks or auxiliaries, as a result of a leak in the reactor cooling or in the condensers used in the fractional condensation, or because of a steam leak into the process in the apparatuses heated directly with steam.

To clean the reactor, the emptied reactor is preferably filled with sodium hydroxide solution (e.g. 5% by weight in demineralized water) which has been heated to about 80° C. and the solution is circulated in the reactor. The cooled aqueous alkali remaining after the cleaning is discarded, optionally after a suitable treatment for release into a wastewater treatment unit (for example a water treatment plant). After the reactor has been cleaned, especially freed of organic soiling, residues of the solution in the reactor system or further cleaned plant components may be removed by means of flushing with water.

Isobutene is highly flammable and in the presence of oxygen can form explosive mixtures, which can ignite at hot surfaces in the presence of particular oxygen concentrations. In standard operation, the plant is suitably operated in startup and shutdown operations in such a way that the oxygen concentration in the gas phase at any time is below the oxygen concentration required for an explosion. For this purpose, the plant is purged and filled prior to startup preferably with an oxygenous gas having an oxygen content of 10% by volume of oxygen or less, preferably 6% by volume of oxygen or less, in a mixture with an inert gas, preferably nitrogen. Preferably, the oxygenous gas is what is called lean air having an oxygen content of 10% by volume of oxygen or less, produced, for example, by suitable dilution of air with molecular nitrogen, for example. All components to be supplied to the process are preferably fed in under a lean air atmosphere. Complete exclusion of oxygen is undesirable particularly when one of the stabilizers elucidated hereinafter requires oxygen to be effective. If oxygen is consumed during the process, fresh lean air is preferably fed in continuously at suitable points, for example into the bottom of the distillation apparatus. The use of lean air prevents the gas composition from passing through an explosive range even in the event of inhomogeneities in the composition of the gas phase.

In order to detect leaks of air, especially into plant components operated under reduced pressure, online oxygen meters are preferably installed at various points in the plant. More preferably, these online oxygen meters are installed in the lines for the noncondensable vapors from the fractional condensations.

The reactor is completely filled with liquid and is therefore preferably safeguarded against thermal expansion by a safety valve. In addition, the reactor preferably has a rapid isolation, emptying and decompression system (SAEES), by means of which the entire reactor contents, in the event of a leak, can be discharged without contact with the environment into a vented collecting vessel which is ventilated and evacuated safely in terms of the explosion risk. The contents of this collecting vessel can preferably be cooled by means of a heat exchanger, in order to be able to remove heat optionally arising from further reaction in a controlled manner. The collecting vessel and its dedicated devices are configured in such a way that the contents thereof can preferably be fed back to the process at various points.

The carboxylic acids used in the present process, when they are carboxylic acids having ethylenically unsaturated groups, may have a high tendency to polymerize, particularly at relatively high temperature. Especially in the case of distillations, these compounds are generally exposed to temperatures which can easily trigger an unwanted free-radical polymerization. This firstly results in the soiling of the apparatus, the blockage of lines and pumps, and deposition on column trays and heat exchange surfaces. The cleaning of the plants is an inconvenient, costly and environmentally polluting operation, and the availability of the plants is greatly reduced as a result. Secondly, uncontrolled free-radical polymerizations can constitute a safety risk. The use of suitable stabilizers can prevent polymerizations of this kind.

To inhibit polymerization, stabilizers or inhibitors are typically used. These stabilizers are typically solids and are fed to the process in solution. The stabilizer solutions are preferably prepared batchwise.

Suitable stabilizers are, for example, N-oxyl compounds, nitroso compounds, phenol compounds, phenothiazines or mixtures thereof. The polymerization-inhibiting action of the stabilizers is generally enhanced by the presence of molecular oxygen. In some cases, the presence of molecular oxygen is absolutely necessary for the efficacy of the stabilizer. It is therefore preferable that molecular oxygen is present in the plant.

Suitable N-oxyl compounds include 1-oxyl-2,2,6,6-tetramethylpiperidine (TEMPO), 1-oxyl-2,2,6,6-tetramethylpiperidin-4-ol (4-HT), 1-oxyl-2,2,6,6-tetramethylpiperidin-4-one, 1-oxyl-2,2,6,6-tetramethyl-4-n-propoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)- piperidine; 1-oxyl-2,2,6,6-tetramethylpiperidin-4-yl stearate, 1-oxyl-2,2,6,6-tetra-methylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, 1-oxyl-2,2,6,6-tetramethyl-4-allyloxypiperidine, 1-oxyl-2,2,6,6-tetramethyl-4-acetamidopiperidine, 1-oxyl-2,2,6,6-tetramethyl-4-(N-butylformamido)piperidine, N,N'-bis(1-oxyl-2,2,6,6-tetramethyl-piperidin-4-yl)adipamide, N-(1-oxyl-2,2,6,6-tetramethylpiperidin-4-yl)caprolactam, N-(1-oxyl-2,2,6,6-tetramethylpiperidin-4-yl)-dodecylsuccinimide, 2,4,6-tris-(N-butyl-N-(1-oxyl-2,2,6,6-tetramethylpiperidin-4-yl]-s-triazine, 4,4'-ethylenebis(1-oxyl-2,2,6,6-tetramethyl-piperazin-3-one), 1-oxyl-2,2,6,6-tetramethyl-4-(2,3-dihydroxypropoxy)piperidine, 1-oxyl-2,2,6,6-tetramethyl-4-(2-hydroxy-4-oxapentoxy)piperidine, di-tert-butylnitroxyl and 4,4',4"-tris-(2,2,6,6-tetramethylpiperidinooxyl) phosphite.

1-Oxyl-2,2,6,6-tetramethylpiperidin-4-ol (4-HT) is particularly suitable.

Suitable nitroso compounds include nitrosophenol, N-nitrosodiphenylamine, isoamyl nitrite, N-nitrosocyclohexylhydroxylamine, N-nitroso-N-phenylhydroxylamine and salts thereof.

Suitable phenol compounds include hydroquinone, 2-methoxyphenol, 3-methoxyphenol, 4-methoxyphenol (MEHQ), 2-ethoxyphenol, 3-ethoxyphenol and 4-ethoxyphenol. 4-Methoxyphenol (MEHQ) is particularly suitable.

Suitable phenothiazines comprise phenothiazine (PTZ), 2-methylphenothiazine, 2-octylphenothiazine, 2-nonylphenothiazine, 2,8-dimethylphenothiazine, 3,7-dimethyl-phenothiazine, 3,7-diethylphenothiazine, 3,7-dibutylphenothiazine, 3,7-dioctylpheno-thiazine and 2,8-dioctylphenothiazine, 3,7-dinonylphenothiazine, 2,8-dinonylpheno-thiazine, 2-(α,α-dimethylbenzyl)phenothiazine, 3,7-bis(α,α-dimethylbenzyl)pheno-thiazine and 2,8-bis(α,α-dimethylbenzyl)phenothiazine. Phenothiazine (PTZ) is particularly suitable.

It is also possible to use a plurality of stabilizers at once. The stabilizers are generally employed in amounts of about 2 to 2000 ppm, based on the total amount of carboxylic acid and isobutene.

In a preferred manner, the stabilizer is added in solution in a solvent. Suitable solvents in principle are all of those in which the particular stabilizer is soluble and which is miscible with the liquid phase to be stabilized. In order to avoid contamination with (external) solvents not required in the process in the first place, or the requirement for removal of an external solvent, the solvent used is preferably a liquid present in the process in any case. Particular preference is given to using the pure target ester as solvent.

The stabilizer is typically introduced by quantitatively controlled supply by means of pumps; preferably, the stabilizer solution, for better distribution, is sprayed in by means of spray devices such as spray nozzles.

Some of the stabilizers mentioned are effective only in the presence of oxygen, one example being MEHQ, as a result of which a relatively high oxygen concentration as present in air, for example, would be advantageous. On the other hand, the oxygen concentration should be limited to comparatively low values in order that no explosive mixtures occur. The process is suitably conducted in such a way that the oxygen concentration in the gas phase at all relevant points and at any time is below the explosion limit. The volume ratio of oxygen to nitrogen in all the gaseous mixtures which occur in stages a) to d) is preferably in the range from 0.03 to 0.11.

The tendency to polymerize exists particularly in the liquid phase at reduced concentrations of stabilizers and optionally oxygen. Since the stabilizers are generally nonvolatile, they accumulate in the bottom of the particular evaporation system in evaporation steps. It is therefore normally necessary to add stabilizer again after the evaporation of polymerizable compounds when the compounds are condensed, since the condensate is generally obtained very substantially free of stabilizers.

The process of the invention encompasses a multitude of process steps in which substance mixtures having very different compositions are present under a wide variety of different process conditions. To ensure safe and economically viable operation, it is necessary to vary the stabilizers added in each case, which are introduced into the process at various points.

In a preferred embodiment, in the case of reaction of the carboxylic acid with isobutene, a stabilizer selected from phenothiazines, more preferably PTZ, is present. The (meth)acrylic acid used may already have been pre-stabilized with PTZ, which is advantageous especially in the startup of the plant. Further amounts of PTZ can be metered into the reactor. In the partial evaporation of the esterification mixture to remove the acidic catalyst, PTZ is distilled over into the liquid high boiler phase, which is separated from the product-containing main stream. The liquid high boiler phase is preferably recycled back into the reactor, such that it is generally necessary to supply the process continuously only with small supplementary amounts of fresh PTZ.

In a preferred embodiment, a stabilizer selected from N-oxyl compounds is added in the steps of condensation. More preferably, a solution of 4-HT in target ester is added. The stabilizer is preferably added at the vapor entry into the condenser—at the vapor entry into the first condenser in the case of two-stage partial condensation. Together with a recycle stream of the condensate at the vapor entry of the second condenser, this stabilizer also passes into the second condenser.

The low-boilers distillation column is likewise preferably stabilized with a stabilizer selected from N-oxyl compounds, more preferably 4-HT. The feed stream into the low-boilers distillation column comprises 4-HT from the preceding step, and a further amount of 4-HT is added at the top of the low-boilers distillation column, especially at the vapor entry of the first condenser, and passes into the low-boilers distillation column as well together with the condensate reflux.

In a preferred embodiment, a stabilizer selected from N-oxyl compounds, more preferably 4-HT, is added to the feed to the distillation apparatus.

The bottom and the stripping section of the distillation apparatus are stabilized by the N-oxyl compound. It is preferable not to stabilize the rectifying section of the distillation apparatus with N-oxyl compounds, since it would not be possible to entirely prevent such compounds from passing over. The N-oxyl compounds are undesirable in the target ester because they can lead to discoloration of the product and substances produced therefrom. Therefore, in the rectifying section of the distillation apparatus, a stabilizer selected from phenol compounds, especially MEHQ, is added. This stabilizer is also used for stabilization of the product and therefore does not have any adverse effect, and need not be removed in a later step. MEHQ is preferably added to the circulation stream via the condensers and/or to the condensate reflux stream into the distillation apparatus. Appropriately, this is accomplished by injection via a nozzle installed centrally in the vapor pipe outlet.

In order to ensure the efficacy of the MEHQ, a molecular oxygen-comprising gas, preferably lean air (5% by volume of oxygen in nitrogen), is preferably fed into the bottom of the distillation apparatus. These measures make it possible to prevent polymer formation in the condensers, the vapor pipes and the distillation apparatus, or at least to prevent it to such an extent that economically advantageous long operation run times without shutdowns for cleaning are possible.

The invention is illustrated in detail by the appended figures and the examples.

Figure 1:
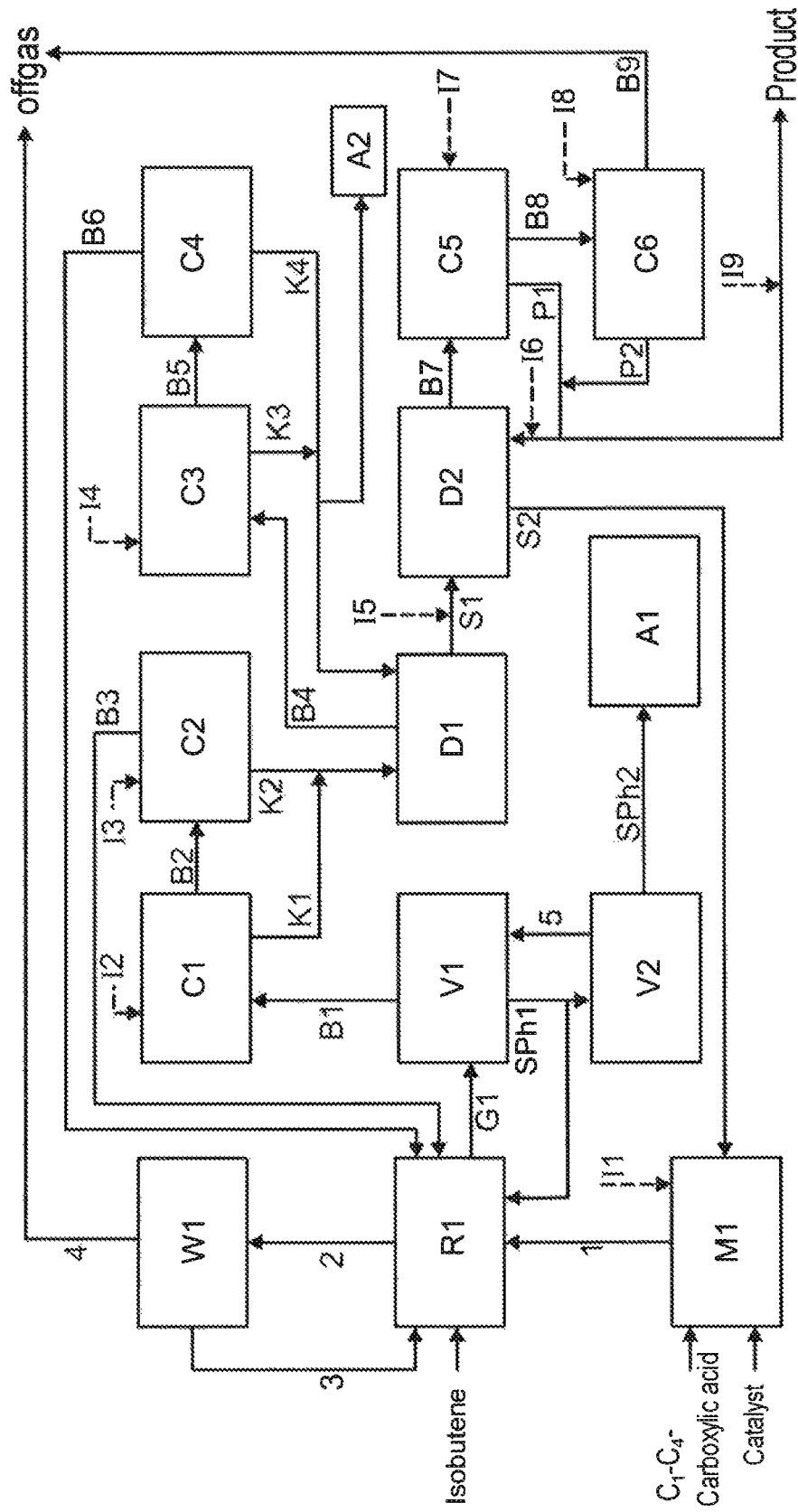
FIG. 1 is a schematic diagram of a plant suitable for implementing the process of the invention.

According to FIG. 1, by means of a mixer M1, an aliphatic $C_1$-$C_4$ carboxylic acid, a stabilizer I1 and the acidic catalyst are fed as a mixture to reactor R1 via a line 1 and a nozzle E1 (not shown in FIG. 1). Isobutene is introduced into the bottom of reactor R1. Via the nozzle E1, the reactor R1 is also supplied with the isobutene-containing uncondensed vapors B3 and B6 from condensers C2 and C4. The condensate from the reflux condenser W1 is fed to reactor R1.

In the reactor R1, the addition reaction of isobutene and the aliphatic $C_1$-$C_4$ carboxylic acid takes place. The reactor has four cooled reaction zones. The reaction zones are separated from one another by dividing sheets, the transition from one reaction zone to the next consisting of a hole of low cross section. The reactants are mixed in the reactor by means of the nozzle E1 and by swirling at the transition from one zone to the next.

The liquid reaction product G1 is drawn off at the top of the reactor R1 by means of a level regulator, so as to establish a constant liquid/gas phase boundary. The gas phase consisting essentially of inert gases, isobutene and small amounts of the tert-butyl ester is fed to the reflux condenser W1 via line 2. The condensate from the reflux condenser W1 comprises isobutene and acrylic acid and is fed via line 3 to reactor R1. The gas phase from the reflux condenser W1 is discharged from the process as offgas via line 4.

The liquid reaction product G1 is drawn off from the side at the top of reactor R1 and fed under quantitative control to the evaporation unit V1 consisting of a falling-film evaporator and a separation vessel (not shown individually in FIG. 1). The pressure of the liquid reaction product is lowered by means of a throttle valve (not shown in FIG. 1) from reactor pressure to reduced pressure, at which the catalyst removal that follows is effected. In the falling-film evaporator of the evaporation unit V1, the reaction mixture is partially evaporated and conducted onward into the separation vessel. The separation vessel preferably comprises a droplet separator in order to reliably remove entrained high boiler components such as sulfuric acid and the stabilizer I1. The non-gaseous constituents are collected in the separation vessel as the first high boiler phase SPh1 and cooled by means of an external cooler (not depicted in FIG. 1) in order to prevent any reverse reaction of the tert-butyl ester present therein to the carboxylic acid and isobutene.

A portion of the first high boiler phase SPh1 is fed under quantitative control to the thin-film evaporator V2, in order to enable the further removal of carboxylic acid or tert-butyl ester in gaseous form. The gas phase produced in the thin-film evaporator V2 is recycled into the separation vessel of the evaporation unit V1 via line 5, while a portion of the liquid second high boiler phase SPh2 is conducted into the settling vessel A1. Preferably, substreams of the second high boiler phase SPh2 are used to preheat the feed stream to the thin-film evaporator of the evaporation unit V1. By varying the hot substreams, it is possible to vary the composition of the feed stream to the thin-film evaporator of the evaporation unit V1 and the temperature of the feed stream.

A further portion of the first high boiler phase SPh1 and a further portion of the second high boiler phase SPh2 are recycled into reactor R1 together or in each case individually under quantitative control via the nozzle E1 (the recycling of the second high boiler phase SPh2 is not depicted in FIG. 1).

The gaseous constituents from the separation vessel of the evaporation unit V1 are fractionally condensed in condensers C1 and C2, the vapor B2 from condenser C1 being conducted into condenser C2. A stabilizer I2 is added at the top of the condenser C1 and a stabilizer I3 is added at the top of the condenser C2. For the cooling of the condenser C1, it is possible to use, for example, river water or cooling water brought to the same temperature level, while condenser C2 is operated with brine cooling. The vapor B3 not condensed in the condenser C2 is conducted into the reactor R1 via nozzle E1.

The condensates K1 and K2 obtained in the condensers C1 and C2 are combined and fed to the side of the distillation column D1. In the distillation column D1, low boilers, particularly diisobutene and isobutene, are removed. The bottom of the distillation column D1 is heated by means of a circulation evaporator (not shown in FIG. 1), by means of which a portion of the bottoms is pumped in circulation. The low boilers B4 are removed in vaporous form at the top of the distillation column D1 and fractionally condensed in the condensers C3 and C4. The vapor B5 from the condenser C3 is conducted into the condenser C4. For the cooling of the condenser C3, it is possible, for example, to use river water or cooling water brought to the same temperature level, while condenser C4 is operated with brine cooling. The vapor B6 uncondensed in the condenser C4 is conducted via the nozzle E1 into the reactor R1. A stabilizer I4 is added at the top of the condenser C3. The condensates K3 and K4 obtained in the condensers C3 and C4 are combined; a substream is conducted into the distillation column D1 as reflux stream, and the remainder is fed to the settling vessel A2.

The bottom stream S1 from the distillation column D1 is fed to the side of the distillation column D2. Stabilizer I5 is metered into the feed to the distillation column D2. The bottom of the distillation column D2 is heated by means of a circulation evaporator (not shown in FIG. 1), through which a portion of the bottoms is pumped in circulation. In the course of pumped circulation, the bottom of the distillation column D2 is also supplied with lean air.

In the distillation column D2, the tert-butyl ester is separated from the remaining aliphatic carboxylic acid. Typically, the boiling point of the carboxylic acid is above the boiling point of the tert-butyl ester, and for that reason the pure tert-butyl ester is drawn off via the top and the carboxylic acid is obtained at the bottom of the distillation column D2. In order to avoid condensation of the tea-butyl ester at the top of the column, the top of the column is heated with steam. Thus, polymerization of the tert-butyl ester optionally resulting from the condensation is also prevented. The bottom stream S2 from the distillation column D2 is recycled into the reactor R1 via a heat exchanger (not shown in FIG. 1) and optionally via a filter (not shown in FIG. 1). The filter may be provided with a bypass line in order to allow it to be taken out or cleaning or for replacement without interruption to the process.

The vapor B7 from the distillation column D2 is fractionally condensed in condensers C5 and C6; the vapor B8 from condenser C5 is conducted into condenser C6. A stabilizer I7 is added at the top of the condenser C5 and a stabilizer I8 is added at the top of the condenser C6. The vapor B9 uncondensed in the condenser C6 is discharged from the process as offgas. The offgas is sent, for example, to a flare or an offgas incinerator.

A substream of the combined condensates P1 and P2 from condensers C5 and C6 is introduced into the condensers C5 and C6 (not depicted in FIG. 1) or, with addition of the stabilizer I6, as reflux stream into the distillation column D2. A further substream of the combined condensates P1 and P2 from the condensers C5 and C6 is discharged from the process as pure tert-butyl ester via a heat exchanger (not depicted in FIG. 1). For storage stabilization, further stabilizer I9 can be added to the pure tert-butyl ester.

The plant preferably has a rapid isolation, emptying and decompression system (SAEES), by means of which, in the event of a leak, the entire contents of the reactor R1 can be discharged into a vented collecting vessel (not shown in FIG. 1). The contents of this collecting vessel can be cooled by means of a heat exchanger, in order to be able to remove the heat that arises from further reaction. The contents of the collecting vessel can be fed back to the process at various points, especially the reactor R1, the falling-film evaporator V2 or the thin-film evaporator of the evaporation unit V1.

Figure 2:
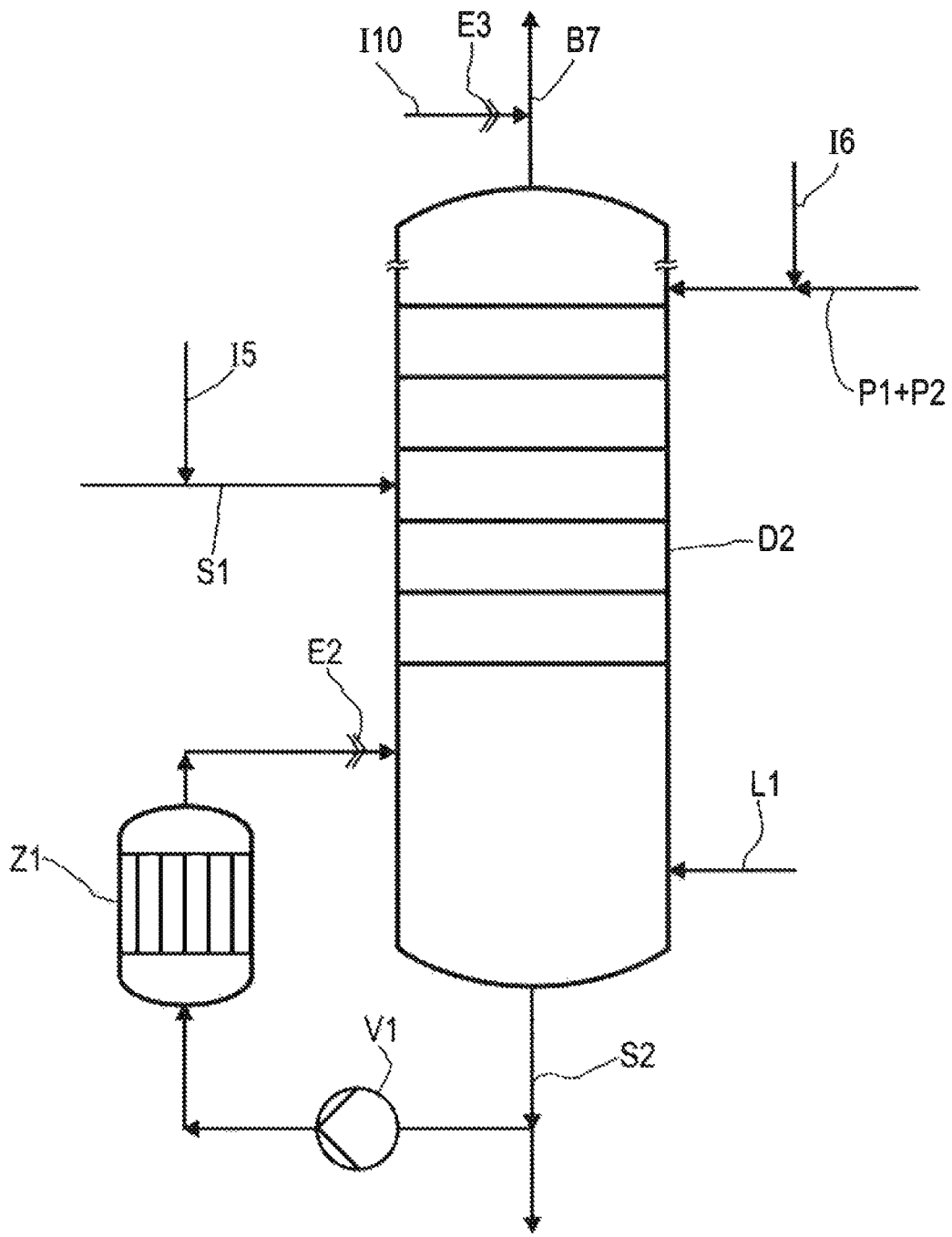
FIG. 2 is a schematic diagram of a distillation apparatus suitable for implementing the purifying distillation.

FIG. 2 is a preferred embodiment of FIG. 1. According to FIG. 2, the bottom stream S1 from the distillation column D1 is fed to the side of the distillation column D2. Stabilizer I5 is metered into the feed of the distillation column D2. A substream of the combined condensates P1 and P2 from the condensers C5 and C6 (not depicted in FIG. 2) is supplied, with addition of the stabilizer I6, as a recycle stream to the distillation column D2.

The bottom of the distillation column D2 is heated by means of a forced circulation evaporator Z1, through which a portion of the bottoms S2 is pumped in circulation by means of the pump V1. The heated stream from the circulation evaporator is recycled via a nozzle E2 into the distillation column D2. The bottom of the distillation column D2 is supplied with lean air L1.

In the distillation column D2, the tert-butyl ester is separated from the remaining aliphatic carboxylic acid. Typically, the boiling point of the carboxylic acid is above the boiling point of the tert-butyl ester, and for that reason the pure tert-butyl ester is drawn off via the top and the carboxylic acid is obtained at the bottom of the distillation column D2. In to avoid condensation of the tert-butyl ester at the top of the column, the top of the column is heated with steam. Thus, polymerization of the tert-butyl ester optionally resulting from the condensation is also prevented. This polymerization is further prevented by the metering of an inhibitor I10 into the vapor pipe B7 by means of a nozzle D3.

EXAMPLE 1

The example which follows was conducted in a plant according to FIG. 1. All the percentages stated are based on weight, unless stated otherwise. Methacrylic acid and isobutene were converted to tert-butyl methacrylate with addition of sulfuric acid. The plant was purged and filled with lean air (5% by volume of oxygen in nitrogen).

Methacrylic acid (MAA, 99.97%, 0.012% acetic acid and 0.011% propionic acid, 575 kg/h) was mixed in a mixer M1 with the methacrylic acid recycled from the bottom of distillation column D2 (91.35% MAA, 5.15% high boilers, 3.32% TBMA, 485 kg/h) and with a phenothiazine (PTZ) solution (97.97% MAA, 2.10% PTZ, 0.01 m$^3$/h) as stabilizer I1. Sulfuric acid (technical grade 96%, 3.7 kg/h) was metered in by means of nitrogen (3.5 bar abs.). Also fed to the mixture was a substream (1500 kg/h) of the liquid phase from the separation vessel of the evaporation unit V1.

The liquid reactants and return streams were fed as a mixture via line 1, a cooler (shell and tube system, 180 m$^2$, 1.4571 stainless steel, not shown in FIG. 1) and nozzle E1 to reactor R1, a cascaded bubble column. The cooler exit temperature was 33° C.

Isobutene (402 kg/h) was metered directly into the bottom of the reactor. Also metered into reactor R1, via the nozzle E1, were the isobutene-containing vapors B3 and B6 from condensers C2 and C4 (122 m$^3$/h), together with the tert-butyl methacrylate-containing condensate from the reflux condenser W1. The nozzle E1 was an ejector jet nozzle. In the nozzle, the pressure was increased by the motive jet to about 2 bar abs.

The reactor R1 had four reaction zones, and the transition consisted of a hole of small cross section (diameter 24 mm). The reaction zones were each cooled (zone 1: external river water cooler, 121 kW; zone 2: external brine cooler, 28 kW; zone 3: internal brine cooler, 14 kW; zone 4: internal brine cooler, 14 kW; the temperature of each of the brines was −20° C.). In the reactor R1, the slightly exothermic addition reaction (−37.6 kJ/mol) of isobutene and methacrylic acid took place at a temperature of 35° C. in zone 1, 25° C. in zone 2, 20° C. in zone 3 and 16° C. in zone 4, and a pressure of 1.92 bar abs.

The reactants were mixed in the reactor firstly by means of the nozzle E1 and secondly by means of swirling at the transition from one zone to the next. At the top of the reactor (zone 4), by means of closed-loop level control, a liquid/gas phase boundary was established.

The gas phase comprised 41.18% isobutene, 0.74% tert-butyl methacrylate (TBMA) and inert gases, and was conducted into the reflux condenser W1 via line 2. The TBMA entrained in the offgas was condensed out by means of reflux condenser W1 and recycled into the reactor R1 via line 3 in a mixture with the isobutene-containing vapors from condensers C2 and C4 via nozzle E1. The pressure at the top of the reactor R1 in the offgas line was adjusted to 1.21 bar abs. At the bottom of the reactor, a pressure of 1.92 bar abs. was established. The gaseous constituents from the reflux condenser W1 (4.37 m³/h) were discharged from the process via line 4.

The liquid reaction product from reactor R1 had the following composition:
    8.58% isobutene
    41.63% MAA
    44.00% TBMA
    0.68% diisobutene
    2.66% high boilers
    2.10% sulfuric acid
    0.35% other constituents The liquid reaction product from the reactor R1 (3.39 m³/h, 16° C.) was removed at the upper end of the reactor R1 and fed via a screen basket filter (0.1 m², not depicted in FIG. 1) to the falling-film evaporator (71.5° C., 309 kW, 47 m²) of the evaporation unit V1. By means of a closed-loop control valve (flow regulation), the pressure was reduced to 60 mbar abs. A biphasic mixture formed as a result of the evaporation of a portion of the low boiler components. In the falling-film evaporator of the evaporation unit V1, the biphasic mixture was evaporated further under temperature control at 55.2° C. and 70 mbar abs. and then passed into the separation vessel of the evaporation unit V1. The separation vessel was equipped with a droplet separator in order to reliably remove sulfuric acid and PTZ.

The non-gaseous constituents in the separation vessel of the evaporation unit V1 were cooled to 2° C. by means of a brine cooler via a pumped circulation stream as the first high boiler phase SPh1. In the separation vessel, accordingly, a mixing temperature of about 8 to 10° C. was established. A portion of the pumped circulation stream (1500 kg/h) of the first high boiler phase SPh1 was fed back to the reactor R1 for sulfuric acid recycling. In addition, a portion of the pumped circulation stream of the first high boiler phase SPh1 (82 kg/h) was fed to the thin-film evaporator V2 (4 m², nickel-chromium-molybdenum alloy 2.4610), in order to remove further products of value (TBMA, MAA) via the top of the thin-film evaporator V2 (89° C., 70 mbar abs.). The thin-film evaporator V2 was heated by means of low-pressure steam. Connected down-stream of the bottoms output of the thin-film evaporator V2 was a pump (not shown in FIG. 1), which conducted the second high boiler phase SPh2 for discharge in a substream to the settling vessel A1. On the way to the settling vessel A1, the substream of the second high boiler phase SPh2 was cooled from 89° C. to 35° C. This was effected by means of a jacketed pipe through which water at a temperature of 30° C. was conducted in countercurrent.

A further substream of the second high boiler phase SPh2 from the thin-film evaporator V2 was in turn admixed as a hot recycle stream directly to the feed stream to the thin-film evaporator V2. By varying the hot recycle stream flow rate, it was possible to adjust the feed stream and the feed stream temperature within a wide range. In conjunction with the adjustment of the amount of heating steam and the heating steam temperature, the thin-film evaporator V2 was capable of covering a large load range.

Yet a further substream of the second high boiler phase SPh2 from the thin-film evaporator was added to the cold pumped circulation stream from the suction side of the pump to the thin-film evaporator V2, but the latter was warmed only to a minor degree as a result. The feed stream to the thin-film evaporator V2 was withdrawn on the pressure side of the pump.

The vapor from the thin-film evaporator V2 was fed via line 5 to the separation vessel of the evaporation unit V1. The vapor B1 from the separation vessel of the evaporation unit V1 (about 68° C.) had the following composition:
    57% TBMA
    24% MAA
    16% isobutene
    3% other constituents The vapor B1 was fractionally condensed and, for this purpose, passed into the top of the condenser C1 (shell and tube heat exchanger, 75 m², cooling: river water (27° C.), 60 mbar abs., 1.4571 stainless steel). In the condenser C1 the mixture fed in was cooled to 29° C.

The vapor B2 from the condenser C1 (comprising about 35% TBMA, 5% MAA, 60% isobutene) was conducted into the top of the condenser C2 (shell and tube heat exchanger, 30 m², cooling: cooling brine (−20° C.), 60 mbar abs., stainless steel 1.4571). The condensate K2 from the condenser C2 (comprising about 86% TBMA, 5% MAA, 4% isobutene, about −17° C.) was combined in a vessel (not shown in FIG. 1) with the condensate K1 from the condenser C1. The vapor B3 from the condenser C2 (comprising about 95% isobutene) was mixed by means of a pump (not shown in FIG. 1) with the vapor B6 from the condenser C4 and recycled into the reactor R1.

The condensate K1 from the condenser C1 (comprising about 68% TBMA, 28% MAA, 0.7% isobutene) was combined in a vessel (not shown in FIG. 1) with the condensate K2 from the condenser C2. The combined condensate from C1 and C2 had the following composition:
    68.09% TBMA
    28.17% MAA
    1.13% diisobutene
    0.74% isobutene
    0.61% other constituents A substream of the combined condensates from C1 and C2 was passed together with a 4-hydroxy-TEMPO (4-HT) solution (2% in TBMA) as stabilizer 12 into the top of the condenser C1, and a substream thereof in turn was passed as stabilizer 13 into the top of the condenser C2.

A further substream of the combined condensates from condensers C1 and C2 was fed to the distillation column D1 (40 dual-flow trays, 91° C. in the column bottom, 120 mbar abs. in the column head) to tray 23. The distillation column D1 was heated by means of a natural circulation evaporator (4 bar abs. steam). The temperature of the distillation column D1 was regulated by means of a regulating valve in the reflux line. The vacuum was regulated by means of a regulating valve in the suction line to the vacuum unit.

The vapor B4 from the distillation column D1 was fractionally condensed and, for this purpose, passed into the condenser C3 (shell and tube heat exchanger, 110 m², cooling: river water (27° C.), 120 mbar abs., 1.4571 stainless steel). In the condenser C3, the mixture fed in was cooled to 29° C. The condensate K3 from condenser C3 was combined in a vessel with the condensate K4 from condenser C4.

The vapor B5 from condenser C3 was passed into condenser C4 (shell and tube heat exchanger, 8 m², cooling: cooling brine (−20° C.), 120 mbar abs., 1.4571 stainless steel) and cooled to −2° C. The condensate K4 from condenser C4 was combined in a vessel (not shown in FIG. 1) with the condensate K3 from condenser C3. The vapor B6 from condenser C4 (65.12 m³/h, 62.94% isobutene) was mixed by means of a pump (not shown in FIG. 1) with the vapor B3 from condenser C2 and the condensate from the reflux condenser W1 and recycled into the reactor R1.

A substream of the combined condensates C3 and C4 was passed into the top of the distillation column D1; a substream thereof in turn was passed as a mixture with a 4-HT solution (2% in TBMA) as stabilizer 14 into the top of the condenser C3.

The bottom product from distillation column 1 had the following composition:
69.63% TBMA
28.65% MAA
1.72% other constituents The bottom product S1 from distillation column D1 was admixed with a 4-HT solution (2% in TBMA) as stabilizer I5 and fed to the distillation column D2 (40 dual-flow trays, 99° C. in the column bottom, 60 mbar abs. in the column head) to tray 18. The distillation column D2 was heated by means of a circulation evaporator (4 bar abs. steam). This was either a natural circulation or a forced circulation evaporator (see variants 1 to 3). The temperature of the distillation column D2 was regulated by means of a regulating valve in the reflux line. The vacuum was regulated by means of a regulating valve in the suction line to the vacuum unit.

Metered into the bottom of distillation column D2 were 6 $m^3$/h of lean air (5% by volume of oxygen in nitrogen).

The vapor B7 from distillation column D2 (comprising 99.83% TBMA) was fractionally condensed and, for this purpose, conducted into condenser C5 (shell and tube heat exchanger, 72 $m^2$, cooling: river water (27° C.), 60 mbar abs., 1.4571 stainless steel). In condenser C5, the mixture fed in was cooled to 29° C. The condensate P1 from condenser C5 was combined in a vessel (not shown in FIG. 1) with the condensate P2 from condenser C6.

The vapor B8 from condenser C5 was passed into the top of condenser C6 (shell and tube heat exchanger, 12 $m^2$, cooling: cooling brine (−20° C.), 55 mbar abs. 1.4571 stainless steel) and cooled to −17° C. The condensate P2 from condenser C6 was combined in a vessel (not shown in FIG. 1) with the condensate P1 from condenser C5 as the product. The vapor B9 from condenser C6 was discharged from the process by means of a pump (not shown in FIG. 1).

A substream of the combined condensates P1 and P2 from condensers C5 and C6 was passed into distillation column D2 as reflux with addition of 4-methoxyphenol (MEHQ, 2% in TBMA) solution as stabilizer I6. Further substreams of the combined condensates P1 and P2 from condensers C5 and C6 were fed to condensers C5 and C6 respectively with addition of 4-methoxyphenol (MEHQ, 2% in TBMA) solution as stabilizers 17 and 18.

In this case, the stabilization of the column was undertaken with a higher content of MEHQ, while the 4-methoxyphenol content in condensers C5 and C6 was 15+/−5 ppm. In order to avoid the condensation of TBMA at the top of distillation column D2, which could also lead to polymerization of TBMA, the top of the column was heated with steam (4 bar abs.).

Yet a further substream of the combined condensates P1 and P2 from condensers C5 and C6, after the pressure had been increased to 4 bar abs., was cooled to 20° C. by means of a heat exchanger (spiral heat exchanger, cooling: cooling brine (−20° C.), not shown in FIG. 1) and discharged from the process as product. A substream thereof was used as solvent for the 4-HT and MEHQ stabilizers.

The product had the following composition:
99.68% TBMA
0.30% isobutene
100 ppm acid (MAA, acetic acid, propionic acid)
17 ppm MEHQ The bottoms S2 from distillation column D2 (comprising 91.35% MAA), after the pressure had been increased to 4 bar abs., was cooled to 35° C. by means of a heat exchanger (spiral heat exchanger, 5 $m^2$, cooling: warm water, 1.4571 stainless steel, not shown in FIG. 1), and a substream was combined with the feed stream of the methacrylic acid and fed to reactor R1.

The reduced pressure required in the evaporation unit V1 and the downstream units was generated by means of a vacuum unit. Roots piston compressors without lubricant oil were used.

For preparation of the stabilizer solution of phenothiazine, methacrylic acid in pure form was initially charged in a stirred vessel (trace-heated with water, 30° C., vented). PTZ was introduced in solid form into the stirred vessel via a sack emptying station and a pneumatic powder transfer system by means of application of reduced pressure via a pump. Small amounts of lean air (5% by volume of oxygen in nitrogen) were added. PTZ was dissolved while stirring and the PTZ solution was passed into a reservoir vessel (trace-heated with water, 30° C., vented), from which the metered addition into the process was undertaken.

For preparation of the stabilizer solution of 4-hydroxy-2,2,6,6-tetramethyl-1-oxyl-piperidine, tert-butyl methacrylate (from the combined condensates P1 and P2 from condensers C5 and C6) was initially charged in a stirred vessel (vented). 4-HT was introduced in solid form into the stirred vessel via of a sack emptying station and a pneumatic powder transfer system by means of application of reduced pressure via a pump. Small amounts of lean air (5% by volume of oxygen in nitrogen) were added. 4-HT was dissolved while stirring and the 4-HT solution was passed into a reservoir vessel (vented), from which the metered addition into the process was undertaken.

For preparation of the stabilizer solution of 4-methoxyphenol, tert-butyl methacrylate (from the combined condensates P1 and P2 from condensers C5 and C6) was initially charged in a stirred vessel (vented). MEHQ was introduced in solid form into the stirred vessel via of a sack emptying station and a pneumatic powder transfer system by means of application of reduced pressure via a pump. Small amounts of lean air (5% by volume of oxygen in nitrogen) were added. MEHQ was dissolved while stirring and the MEHQ solution was passed into a reservoir vessel (vented), from which the metered addition into the process was undertaken.

The brine used in the brine coolers was set up as a pressure circuit. The brine was cooled in an ammonia refrigeration system to −20° C. and fed to the respective process elements. Thereafter, the brine was homogenized in a brine reservoir and fed by means of a pump back to the ammonia refrigeration system. The brine system had a balancing vessel blanketed with lean air (5% by volume of oxygen in nitrogen).

Unutilizable offgas obtained in the process was conducted through a separator and the uncondensed constituents were incinerated in a shielded flare, while the condensate was discharged.

It is clear that the process allows the preparation of tert-butyl methacrylate in high purity (99.68% here) with simultaneously energetically favorable removal of isobutene, which was isolable with a high level of separation from the esterification mixture.

EXAMPLE 1—VARIANT 1

The process was carried out according to Example 1. The purifying distillation was operated with a natural circulation evaporator (4 bar abs. steam, 114 tubes) and without additional wall heating in the top region.

Temperature at the bottom of the purifying distillation: about 102° C.

Temperature at the top of the purifying distillation: about 58° C.

Wall temperature in the top region: about 53° C.

Reflux ratio: 3.1

Heating steam for the natural circulation evaporator: about 400 kg/h

Differential pressure in the column: about 55 mbar

Figure 3:
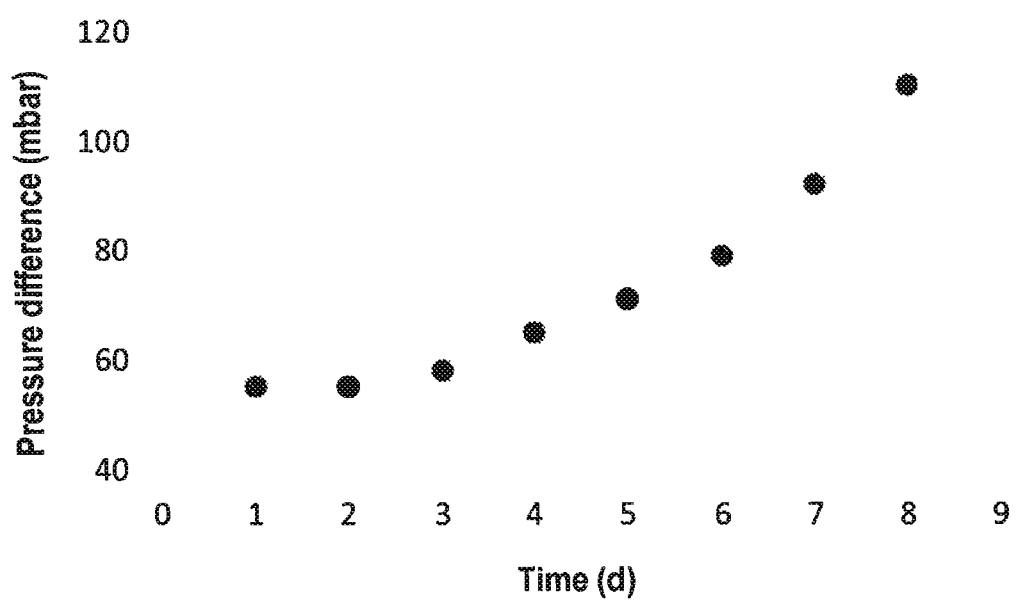
FIG. 3 shows the differential pressure in a distillation apparatus according to FIG. 2, which is operated with a natural circulation evaporator and without heating of the top region of the distillation apparatus, as a function of time.
Figure 4:
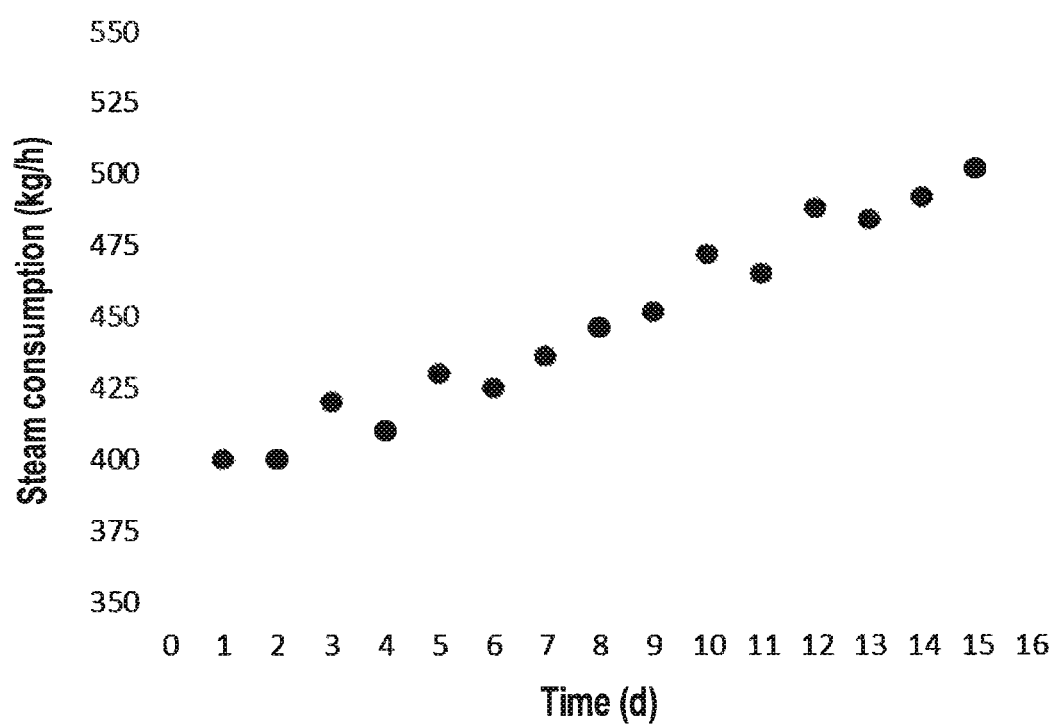
FIG. 4 shows the heating power of a distillation apparatus according to FIG. 2, which is operated with a natural circulation evaporator and with heating of the top region of the distillation apparatus, in the form of steam consumption as a function of time.
Figure 5:
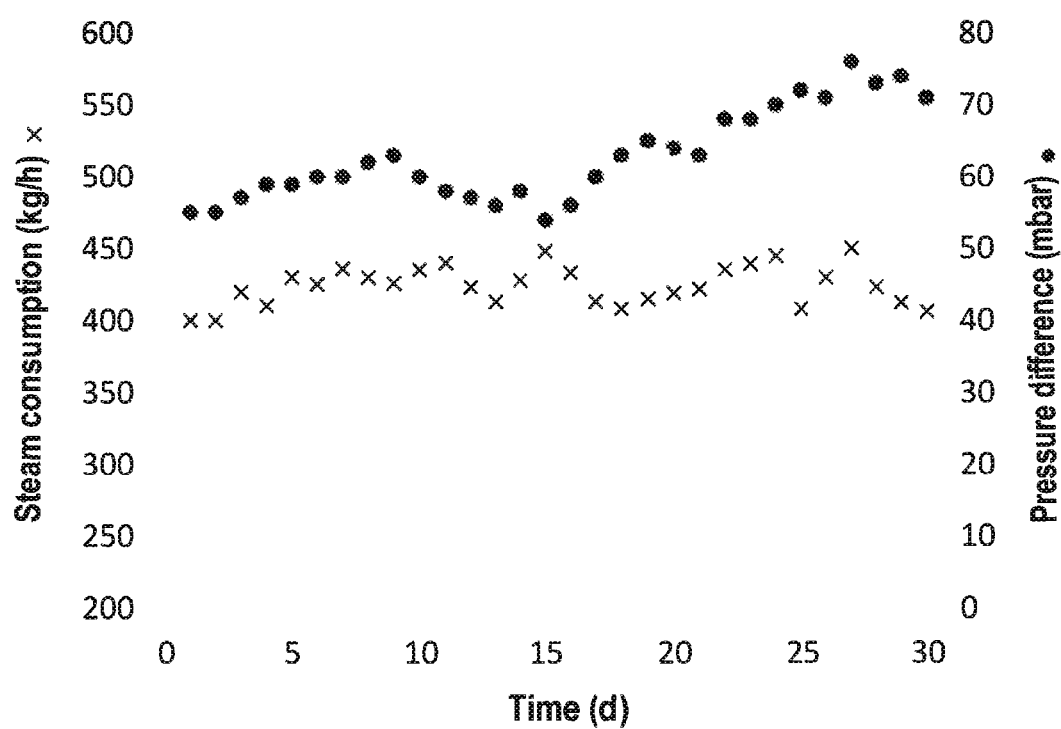
FIG. 5 shows the differential pressure and the heating power (in the form of steam consumption) in a distillation apparatus according to FIG. 2, which is operated with a forced circulation evaporator and with heating of the top region of the distillation apparatus, as a function of time.

The differential pressure in the purifying column D2 was investigated as a function of time. The differential pressure and the heating power are considered to be indicators of the degree of polymerization in the column. An increase in the differential pressure in the purifying column D2 was observed, from about 55 mbar to about 110 mbar, over a period of about 8 days (FIG. 3). The cause of the pressure increase was the condensation of gaseous products on the surfaces in the top region of the column, these products forming unstabilized liquid phases susceptible to polymerization and leading to a covering on the surfaces in the top region of the column.

A decreasing heating performance (heat transition) of the natural circulation evaporator was also found. The quantity of heating steam required increased from about 400 kg/h to about 500 kg/h.

The top two trays of the column were removed and required cleaning, being covered with polymer chunks. Approximately 30% of the internal evaporator tubes were clogged with polymer, and likewise required cleaning, which was costly and laborious.

EXAMPLE 1—VARIANT 2

The process was carried out according to Example 1. The purifying distillation was operated with a natural circulation evaporator (4 bar abs. steam, 114 tubes) and with wall heating in the top region by means of jacketing with a half-coil pipe (110° C., 1.5 bar).

Temperature at the bottom of the purifying distillation: about 102° C.

Temperature at the top of the purifying distillation: about 58° C.

Wall temperature in the top region: about 66° C.

Reflux ratio: 3.1

Heating steam for the natural circulation evaporator: about 400 kg/h

Differential pressure in the column: about 55 mbar

The heating power of the natural circulation evaporator was investigated as a function of time. The heating power is considered to be an indicator of the degree of polymerization in the column. A decreasing heating power (heat transition) of the natural circulation evaporator was found. The quantity of heating steam required increased from about 400 kg/h to about 500 kg/h.

The process had to be interrupted after 15 days. The column top was opened, and a covering of polymer was found neither in the column top nor on the topmost tray. However, about 30% of the internal evaporator tubes were clogged with polymer, and required cleaning, which was costly and laborious.

EXAMPLE 1—VARIANT 3

The process was carried out according to Example 1. The purifying distillation was operated with a forced circulation flash evaporator (4 bar abs. steam, 308 tubes) and with wall heating in the top region by means of jacketing with a half-coil pipe (110° C., 1.5 bar).

Temperature at the bottom of the purifying distillation: about 102° C.

Temperature at the top of the purifying distillation: about 58° C.

Wall temperature in the top region: about 66° C.

Reflux ratio: 3.1

Heating steam for the natural circulation evaporator: about 400 kg/h

Differential pressure in the column: about 55 mbar

The differential pressure in the purifying column D2 and also the heating power of the forced circulation evaporator were investigated as a function of time. The differential pressure and the heating power are considered to be an indicator of the degree of polymerization in the column. Over a period of 30 days, no significant increase was observed in the differential pressure in the purifying column.

The process was interrupted. The column top was opened, and a covering of polymer was found neither in the column top nor on the topmost tray nor in the forced circulation evaporator tubes.

We claim:

1. A process for continuously preparing the tert-butyl ester of an ethylenically unsaturated carboxylic acid, by
   a) reacting an ethylenically unsaturated carboxylic acid with isobutene in the presence of an acidic catalyst to give an esterification mixture;
   b) removing the acidic catalyst;
   c) removing low-boiling components; and
   d) supplying a tert-butyl ester-comprising liquid to a distillation apparatus and subjecting it to purifying distillation in the distillation apparatus, where
   d1) in the distillation apparatus the tert-butyl ester-comprising liquid is separated into a tert-butyl ester-comprising gaseous top product and a carboxylic acid-comprising liquid bottom product;
   d2) the tert-butyl ester-comprising gaseous top product is at least partly condensed and the condensate is recycled partly as reflux to the distillation apparatus;
   d3) the carboxylic acid-comprising liquid bottom product is recycled at least partly to step a);
   d4) carboxylic acid-comprising liquid bottom product is drawn off and passed to a heater; a superheated, liquid recycle stream is taken from the heater; and the superheated recycle stream is let down into the distillation apparatus; and
   d5) at least in the top region of the distillation apparatus, the distillation apparatus walls in contact with the vapor, at least in sub-regions, are heated and/or thermally insulated.

2. The process according to claim 1, wherein the ethylenically unsaturated carboxylic acid is selected from the group consisting of acrylic acid and methacrylic acid.

3. The process according to claim 1, wherein the ethylenically unsaturated carboxylic acid has an acetic acid content of less than 300 ppm and a propionic acid content of less than 300 ppm.

4. The process according to claim 1, where
   d1') the liquid bottom product is guided via an apparatus which frees it from solid impurities.

5. The process according to claim 4, wherein the apparatus is a filter.

6. The process according to claim 1, wherein the heater is a shell and tube heat exchanger which operates in indirect heat exchange against a heating medium.

7. The process according to claim 1, wherein the superheated recycle stream is let down via a flow limiter selected from the group consisting of a baffle, a valve, a constrictor, a perforated plate, a nozzle, a capillary, and combinations thereof.

8. The process according to claim 1, wherein the acidic catalyst is an inorganic acid.

9. The process according to claim 1, wherein the acidic catalyst is an organic acid.

10. The process according to claim 1, wherein the esterification mixture comprises 0.1 to 10 wt % of the acidic catalyst.

11. The process according to claim 1, wherein the reaction in step a) is carried out in the presence of a stabilizer selected from phenothiazines.

12. The process according to claim 1, wherein a stabilizer selected from phenol compounds is metered into the rectifying section of the distillation apparatus.

13. The process according to claim 1, wherein a stabilizer selected from N-oxyl compounds is metered into the feed to the distillation apparatus.

14. The process according to claim 1, wherein the volume ratio of oxygen to nitrogen in all gaseous mixtures which occur in stages a) to d) is in the range from 0.03 to 0.11.

* * * * *